US010265484B2

(12) United States Patent
Stuart et al.

(10) Patent No.: US 10,265,484 B2
(45) Date of Patent: Apr. 23, 2019

(54) DISPENSING ASSEMBLY

(71) Applicant: 3M INNOVATIVE PROPERTIES COMPANY, St. Paul, MN (US)

(72) Inventors: Adam J Stuart, Loughborough (GB); Adam S. Cantor, River Falls, WI (US)

(73) Assignee: 3M INNOVATIVE PROPERTIES COMPANY, St. Paul, MN (US)

( * ) Notice: Subject to any disclaimer, the term of this patent is extended or adjusted under 35 U.S.C. 154(b) by 703 days.

(21) Appl. No.: 14/430,710

(22) PCT Filed: Sep. 24, 2013

(86) PCT No.: PCT/US2013/061298
§ 371 (c)(1),
(2) Date: Mar. 24, 2015

(87) PCT Pub. No.: WO2014/052263
PCT Pub. Date: Apr. 3, 2014

(65) Prior Publication Data
US 2015/0246187 A1    Sep. 3, 2015

Related U.S. Application Data

(60) Provisional application No. 61/706,416, filed on Sep. 27, 2012.

(51) Int. Cl.
*A61M 15/00* (2006.01)
*C09J 7/20* (2018.01)
*C09J 7/38* (2018.01)

(52) U.S. Cl.
CPC .... *A61M 15/0001* (2014.02); *A61M 15/0026* (2014.02); *A61M 15/0065* (2013.01);
(Continued)

(58) Field of Classification Search
CPC ........ C09J 7/02; C09J 7/0207; C09J 2433/00; C09J 2400/24; C09J 2201/622; C09J 2201/28; A61M 15/0026
See application file for complete search history.

(56) References Cited

U.S. PATENT DOCUMENTS 4,965,887 A * 10/1990 Paoluccio ............... A61F 9/02
128/201.25
5,069,512 A * 12/1991 Sykes ..................... A47F 3/005
248/205.3
(Continued)

FOREIGN PATENT DOCUMENTS

AU        740126        7/1999
EP        0439708       8/1991
(Continued)

OTHER PUBLICATIONS

International Search Report for PCT International Application No. PCT/US2013/061298 dated Feb. 13, 2014, 6 pages.

*Primary Examiner* — Gregory A Anderson
*Assistant Examiner* — Victoria Murphy

(57) ABSTRACT

A dispensing assembly for a container filled with a medicinal substance or formulation, the container being suitable for administering the medicinal substance or formulation via inhalation, buccal or sublingual delivery. The dispensing assembly includes a housing (1) defining a patient port through which, in use, the medicinal substance or formulation is dispensed. The dispensing assembly further includes a cap (3) that can be engaged with and disengaged from the patient port to close and open the patient port and an adhesive tape (10) having one portion (12) affixed to the housing and a second portion (11) affixed to the cap, such that when the cap is disengaged from the patient port, the cap is still connected to the housing.

18 Claims, 2 Drawing Sheets

(52) U.S. Cl.
CPC . *C09J 7/20* (2018.01); *C09J 7/38* (2018.01); *A61M 2207/00* (2013.01); *C09J 2201/28* (2013.01); *C09J 2201/622* (2013.01); *C09J 2400/24* (2013.01); *C09J 2433/00* (2013.01)

(56) References Cited

U.S. PATENT DOCUMENTS

| | | | |
|---|---|---|---|
| 5,192,612 A * | 3/1993 | Otter | C08G 63/08 |
| | | | 428/343 |
| 5,209,375 A | 5/1993 | Fuchs | |
| 5,695,837 A * | 12/1997 | Everaerts | C09J 7/0217 |
| | | | 428/317.1 |
| 5,833,093 A | 11/1998 | Honaker | |
| 5,971,214 A | 10/1999 | Bettison, Jr. | |
| 2004/0089292 A1 * | 5/2004 | Pollet | A61M 15/0028 |
| | | | 128/200.23 |

FOREIGN PATENT DOCUMENTS

| | | |
|---|---|---|
| GB | 2272162 | 5/1994 |
| GB | 2312848 | 11/1997 |
| GB | 2323041 | 9/1998 |
| GB | 2348676 | 10/2000 |
| GB | 2364320 | 1/2002 |
| GB | 2419292 | 4/2006 |
| WO | WO 1993-24164 | 12/1993 |
| WO | WO 1996-12661 | 5/1996 |
| WO | WO 1998-41260 | 9/1998 |
| WO | WO 1998-41262 | 9/1998 |
| WO | WO 1998-42395 | 10/1998 |
| WO | WO 1999-04840 | 2/1999 |
| WO | WO 1999-25405 | 5/1999 |
| WO | WO 1999-28042 | 6/1999 |
| WO | WO 2001-47590 | 7/2001 |
| WO | WO 2001-87731 | 11/2001 |
| WO | WO 2002-00279 | 1/2002 |
| WO | WO 2002-04056 | 1/2002 |
| WO | WO 2002-49698 | 6/2002 |
| WO | WO 2002-085436 | 10/2002 |
| WO | WO 2004-041670 | 5/2004 |
| WO | WO 2004-080606 | 9/2004 |
| WO | WO 2005-046774 | 5/2005 |
| WO | WO 2005-087299 | 9/2005 |
| WO | WO 2005-113365 | 12/2005 |
| WO | WO 2006-097756 | 9/2006 |
| WO | WO 2007-028992 | 3/2007 |
| WO | WO 2007-134793 | 11/2007 |
| WO | WO 2010-142418 | 12/2010 |

\* cited by examiner

DISPENSING ASSEMBLY

CROSS REFERENCE TO RELATED APPLICATIONS

This application is a national stage filing under 35 U.S.C. 371 of PCT/US2013/061298, filed Sep. 24, 2013, which claims priority to U.S. Application No. 61/706,416, filed Sep. 27, 2012, the disclosure of which is incorporated by reference in its/their entirety herein.

FIELD

The present invention relates to a dispensing assembly, to a dispensing device and in particular to a dispensing device in the form of a medicinal inhalation device (e.g. a pressurized metered dose inhaler (pMDI) or a dry powder inhaler (DPI), or a portable nebulizing inhaler).

BACKGROUND

Portable inhalers include pMDIs, DPIs and portable nebulizers. They are used to deliver medicinal substance to the lungs, to the nasal passages, to the buccal cavity or sublingually.

pMDIs are well known in the art of inhalation devices. It is therefore not necessary to describe the construction and operation of a pMDI other than in bare essentials.

A pMDI typically comprises a canister and an actuator. The actuator typically includes a tubular housing provided with a patient port, for example a mouthpiece or a nosepiece. The housing is generally formed of a plastics material, for instance by molding (e.g. plastic injection molding). Typical plastics used for actuators are high density polyethylene, polypropylene or poly-acrylonitrile-butadiene-styrene. The canister comprises an open-ended container (typically made from a metal such as aluminum) capped by a metering valve and filled with medicinal aerosol formulation. It is inserted valve-down into the top of the tubular housing so that an outlet stem of the valve engages a nozzle block of the actuator located near the patient port.

In use, a patient in need of a metered dose of the medicinal aerosol formulation concurrently inhales through the patient port and depresses the base of the canister to move the canister from the rest position to the actuated position. The metered dose of the medicinal aerosol formulation is either entrained by the patient's inspiratory airflow into the patient's respiratory tract or nasal passages, or the metered dose of spray impacts directly onto the target organ.

Inhalers are commonly provided with a dust cap, made of the same material as the actuator, which covers the patient port when the inhaler is not in use. The dust cap, when applied, prevents foreign material from entering the housing. This prevents the user from inhaling for example, dust or lint, which might otherwise accumulate in the housing. This is of particular importance where the user suffers from asthma or other respiratory conditions, in which the inhalation of foreign material may cause severe irritation.

However, the dust cap is often lost by the patient, in which circumstance so also is its benefit in respect of subsequent doses to be taken.

Consequently, some inhalers, particularly pMDIs provided for the US market are provided with caps that are attached to actuators by some means.

WO-A-2002/04056 describes embodiments in which the cap is connected to the housing by a strap formed of a thermoplastic elastomer material. The strap is joined to the cap and housing by mechanical fasteners, glue, heated or ultrasonic welds or a combination of these means.

WO-A-2005/046774 discloses an inhaler in which the cap is attached to the actuator by means of a strap. The cap is arranged to slide on the strap, which is co-molded with the actuator.

WO-A-2005/087299 discloses an inhaler in which the cap is attached to the actuator by means of a telescopic strap. The telescopic strap consists of two components; a first component is attached to the cap by a hinge, e.g. a "living hinge", and the second component is attached to the actuator in the same way but optionally also with a hole that fits over a stud on the actuator.

SUMMARY OF THE INVENTION

If such features are to be retrofitted onto existing designs of dispensing devices, modifications to the molding tooling are required, which for established products can be prohibitively expensive to implement.

It would thus be advantageous to provide a means to retrofit attached caps to housings that is economic and robust and without detracting from the quality of appearance of the product.

Accordingly, one aspect of the present invention is a dispensing assembly for containing a container filled with a medicinal substance or formulation, said container being suitable for administering the medicinal substance or formulation via inhalation, buccal or sublingual delivery, wherein the dispensing assembly comprises a housing defining a patient port through which, in use, said medicinal substance or formulation is dispensed, wherein the dispensing assembly further comprises a cap that can be engaged with and disengaged from the patient port to close and open the patient port, and an adhesive tape having one portion affixed to the housing and a second portion affixed to the cap, so that when the cap is disengaged from the patient port, the cap is still connected to the housing.

According to an additional aspect, the invention provides a dispensing device comprising a dispensing assembly as described in the previous paragraph and a container.

Preferably the dispensing device is a pMDI, and then the housing with its patient port is referred to as an actuator.

According to a further aspect, the invention provides a method of manufacture of adhesive tapes suitable for connecting caps to housings of portable inhalers or metered pump sprays, which comprises a) arranging outlines of tapes on a web of tape material, b) applying adhesive to regions of the web across the outlines and c) cutting adhesive tapes from the web.

Preferably the method is suitable for connecting a cap to a housing of a portable inhaler, particularly a pMDI.

DETAILED DESCRIPTION

Figure 1A:
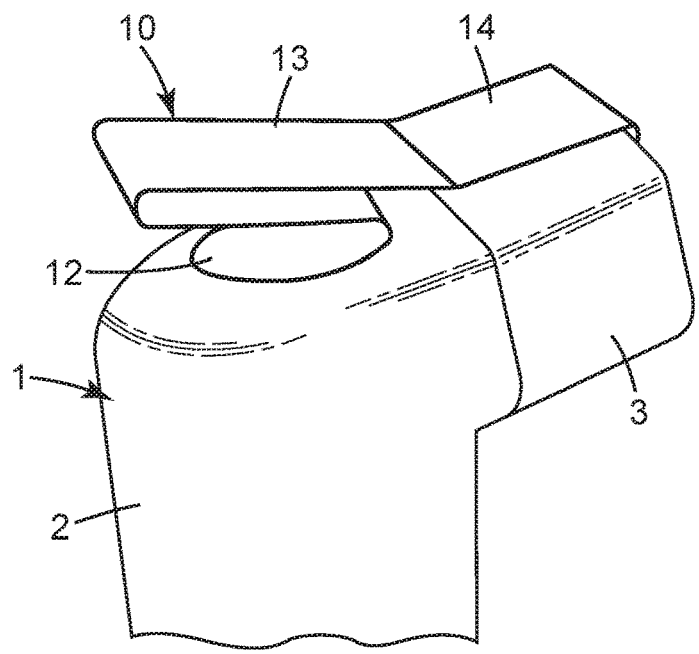
FIGS. 1a and 1b are side views of part of an inhaler in accordance with the invention, shown inverted.

The above summary of the present invention is not intended to describe each disclosed embodiment or every implementation of the present invention. The description that follows more particularly exemplifies illustrative embodiments. Also further embodiments are described in dependent claims. In several places throughout the application, guidance is provided through lists of examples, which examples can be used individually and in various combinations. In each instance, the recited list serves only as a representative group and should not be interpreted as an exclusive list.

It has been found particularly beneficial for a product developed without means to connect a dust cap to the housing, to provide an inhaler that has this feature without the need to make alterations to the molding tooling for the housing or the cap. Thus the invention provides, for example, a simple, low-cost solution for tethering a pMDI actuator cap to its actuator by using a locally adhered tape. The tape used in the invention may be made out of fabric, rubber, a plastic leash, plastic tape, reinforced paper, nonwoven sheet etc., It is convenient if the tape is a pressure sensitive adhesive tape.

Surprisingly it has been found that tapes can be adhered without allowing adhesive to be exposed due to abrupt pull-off forces that could be applied by a patient removing the cap with a follow through movement. Exposed adhesive could contact the patient's mouth during subsequent use which would be undesirable.

A cap used in the invention typically has a short tubular portion, with a closed end and an open end. The tubular portion typically fits flush over the patient port. It may be made from high density polyethylene, polypropylene or poly-acrylonitrile-butadiene-styrene. The tape used in the invention may be adhered to the cap at one or more external surfaces selected from the closed end, a side, a bottom or a top surface, where said top, bottom and side surfaces are on the outside of the tubular portion. Advantageously, it is attached to a whole surface for maximum adhesion, although attachment to a partial surface is possible where sufficient contact area can be provided. Desirably, such partial coverage is arranged not to detract from the appearance of the dispensing device. The tape may be adhered to any extent of flat surface on the outside of the housing. Preferably, it is adhered to a region that adjoins the patient port, as this minimizes the length of tape required. More preferably, the regions of the cap and the housing to which the tape is adhered are adjoining, or in close proximity to each other, which again minimizes the length of tape required and allows the possibility to avoid the tape catching on nearby items.

Suitable adhesives for the adhesive tape may be based on a plurality of polymer base materials. For example, the polymer base material for the polymeric adhesive may independently be selected from the group comprising acrylic resins, natural rubbers, synthetic rubbers, block-copolymers, α-olefin polymers like polyethylene or polypropylene, polyurethanes, polyamines, polyesters, polyethers, polyisobutylene, vinylic compounds, polyamids or combinations thereof.

Acrylate-based precursors are in particular preferred. These precursors may comprise alkyl (meth)acrylate monomers with alkyl groups containing 4 to 20 carbon atoms. Useful alkyl (meth)acrylates include linear and branched monofunctional unsaturated acrylates of alkyl alcohols, the alkyl groups of which have from 4 to 14, preferably from 4 to 10 and, in particular, from 4 to 6 carbon atoms. Useful examples include n-butyl acrylate, isobutyl acrylate, hexyl acrylate, 2-ethylhexyl acrylate, isooctyl acrylate, n-octyl acrylate, 2-methylbutyl acrylate, isononyl acrylate, n-nonyl acrylate, n-decyl acrylate, isodecyl acrylate, isobornyl acrylate, 4-methyl-2-pentyl acrylate and dodecyl acrylate and their methacrylate analogues. Preferred alkyl acrylate esters include isooctyl acrylate, n-butyl acrylate, 2-ethylhexyl acrylate, isononyl acrylate, dodecyl acrylate, 2-propylheptyl acrylate and mixtures thereof. Particularly suitable alkyl acrylates include isooctylacrylate, 2-ethyl hexyl acrylate and combinations thereof.

Acrylic adhesives are formulated from starting materials which may include acrylate-based precursor as described above, including precursor that would polymerize into a material with a glass transition temperature, $T_g$, of less than 0° C. Starting materials could include a copolymerizable monomer, which may be used to adjust the glass transition temperature of the finished adhesive, e.g. by selecting a copolymerizable monomer whose homopolymer has a $T_g$ greater than 15° C., and/or make the acrylate-based precursor miscible with any tackifier present in the starting materials, for example by rendering the starting materials less polar by selecting a copolymerisable monomer whose homopolymer has a Fedors solubility parameter of no greater than 10.50, e.g. an alkyl acrylate such as iso-octyl acrylate and/or isobornyl acrylate, or alternatively N-alkyl acrylamide where the N-alkyl is a $C_{1-8}$ saturated group. However, it may be desirable to make any tackifier less miscible in the finished adhesive to the extent that it phase separates, by adjusting the polarity of the copolymerisable monomer, as this can result in better shear resistance. Desirably, the starting materials include a tackifier e.g. esters of hydrogenated rosin or aromatic hydrogenated hydrocarbon, since tackifier improves the peel adhesion force.

Tackifiers include the following types as exemplified by specific resin products: Regalrez 1085 or Regalrez 6108 hydrocarbon pure monomer resins and Kristalex3100 aromatic pure monomer hydrocarbon resin (available from Eastman Chemical Company, Kingsport, Tenn., USA), Wingtack Plus aromatically modified C-5 hydrocarbon resin (available from Cray Valley USA, Exton, Pa., USA), Arkon E90 or Arkon M90 water-white hydrocarbon resins (available from Arakawa Europe GmbH, Eschborn, Germany).

Preferably, a photoinitiator such as a benzoin ether, e.g. 2,2-dimethoxy-2-phenylacetophenone, and optionally a crosslinking agent e.g. substituted triazines, for example 2,4-bis(trichloromethyl)-6-(4-methoxyphenyl)-triazine, are included as starting materials. The aforementioned starting materials are copolymerized with uv light (90% of emission between 300 nm and 400 nm), preferably in a solvent-free, oxygen-free environment after coating onto a release liner or tape. Preferably, the finished adhesive has a glass transition temperature in the range 0° C. to 10° C., as this property allows the adhesive to conform closely to the attachment surface while also providing some rigidity to enhance the peel force.

The adhesive may be in the form of foam. In this case hollow polymeric microspheres of a size in the range 10 μm to 200 μm are mixed with the starting materials at a concentration of about 15% v/v (volume/volume) to about 75% v/v. Alternatively, adhesive may be laminated onto a polyurethane foam, such as a polyether polyol polyurethane, to provide the effects of an adhesive foam.

The 3M™ 300LSE "Hi-strength" Acrylic adhesive and VHB™ Acrylic foam adhesives are preferred. These are designed for low surface energy materials and will provide a strong bond to the Polypropylene or High Density Polyethylene of housings and caps. 300LSE may be applied to a tape, rubber, plastic, reinforced paper or non-woven material using a transfer tape such as either 9471LE or 9472LE Laminating Adhesives, available from 3M Tapes and Adhesives group, Bracknell, UK. Greater adhesion is provided by 9472LE due to the thicker adhesive layer (127 μm). VHB™ Acrylic foam is available as double-sided, pressure-sensitive, closed-cell acrylic foam tape, such as Heavy Duty Mounting Tape 5952 and Tape 4932, both of which are available from 3M Tapes and Adhesives group, Bracknell, UK. Pressure sensitive adhesive foams, particularly those with closed cells, present a thicker adhesive layer (1.1 mm for 5952 and 0.6 mm for 4932), which provides a better softer feel—for example for the patient's thumb during actuation of an inhaler—but may require an additional surface roughening step to provide a key for the surfaces to which the foam will be adhered.

Suitably, the adhesive, when composed into a prepared specimen and tested according to standard test method ASTM D3330, method E modified to use 90° peel to separate one face of the adhesive from a stainless steel panel instead of the prescribed 180°, the opposing face of the adhesive attached to a 51 micron aluminum backing in place of the prescribed 25 micron polyester film, the prepared specimen stood for a 15 minute dwell time at room temperature prior to testing instead of the prescribed 1 minute, and carrying out the adhesion testing at a rate of peel of 5 mm $s^{-1}$ (as prescribed), gives a peel adhesion of at least 40 N per 100 mm, preferably at least 60 N per 100 mm, more preferably at least 75 N per 100 mm, most preferably at least 80 N per 100 mm.

Suitable tapes include rubber, plastics, non-woven, reinforced paper or a fabric material of thickness 0.2 mm to 2.0 mm depending on the type of material, with greater thicknesses more suitable for foam materials. Thus foams may be 0.5 mm to 2.0 mm thick, preferably 0.5 to 1.2 mm thick; whereas other tapes may be 0.2 mm to 0.5 mm thick so that they may be recessed into already existing features of caps and housings for a more pleasing appearance and less temptation for a patient to pick at them. The length should accommodate comfortable disengagement of the cap without leaving an unwieldy length that could catch on nearby items; accordingly a length (13) uncoated with adhesive is provided that is between 15 mm and 100 mm. Preferably this length is between 30 mm and 50 mm. The width is chosen to confer some degree of inflexibility, to allow the patient to pick up the cap easily in the correct orientation, and provide strength while not requiring extensive areas of flat surface on the original housing and cap for attachment. Accordingly, the width is desirably in the range 10 mm to 20 mm, preferably 12 to 17 mm. The tape may include some reinforcing, such as a mesh of fibers or scrim incorporated into rubber, plastics or paper material to enhance the rigidity. Ideally, the tape material has a low energy surface suitably to bond with the same adhesive as the cap and housing.

The areas of tape to which adhesive is applied are largely determined by the flat areas available on the existing housing, as substantially all such adhesive areas need to be adhered to a surface of a cap or housing. Thus the tape used in the invention advantageously has adhesive applied on only one of its faces. Accordingly, the tape may have a first major face which is free from adhesive, which is the non-adhesive face, and a second major face, which is the opposite face. It is desirable for the tape to have at least 100 $mm^2$ of applied adhesive for each of the cap and the housing. The upper limit is determined by the availability of suitable surfaces and the appearance. Normally, it would be the ends of the tape that are coated with adhesive.

For certain adhesives, it may be desirable to pre-treat the surfaces of the cap and housing to provide a better bond. Thus the surfaces to which the adhesive is required to adhere may be corona treated, flame treated or plasma treated by methods known in the art.

Tapes used in the invention should preferably not be rigid, because non-rigidity may cushion impact that might be applied by the patient when the cap is removed. However, a tape with a low Young's modulus could lead to weakening of the adhesive bond with the cap or housing, or have a tendency to be stretched beyond the elastic limit. Tapes used in the invention may be designed to break before sufficient load could be applied to peel apart the adhesive joint between the tape and either the cap or housing. Such designing could utilize the width, thickness and choice of material, but could include small nicks in the edge of the tape to provide regions of greatest stress where failure could be designed to occur.

It may be desirable to match the color of the tape with that of the housing and/or cap, or to have a contrasting color, or use clear tape and clear adhesive. Since it may not always be clear to an untrained patient how to get access to the medicine when the patient port is covered, potentially causing the patient to use the inhaler irrationally e.g. trying to inhale the cap, contrasting colors help to guide the patient in this respect.

Tapes may be provided with one or more fold lines to cause any loose tape to tend to fold away neatly when the cap is engaged. Fold lines may be provided by folding and applying a high pressure load to the folding region, by applying heat while folding or by scoring. This could be done while the tape is still in web-form.

Preferably the tape is provided with a surface texture on the non-adhesive face which is not smooth. This may allow the patient to grip the base of the housing effectively in use. For example, "NonSkid" textured vinyl (PVC) tape available from Incom Manufacturing group, Ontario, Canada, or ultra grip texture bicycle handlebar tape available from Serfas, Rancho Santa Margarita, Calif., USA, or anti-slip high traction safety tape (normally used to provide grip to treaded surfaces in a work environment) from C. R. Laurence of Europe Ltd., Rochdale, UK, could be used. Another possible surface texture could be provided using Bar Tape from the LizardSkins Company, Orem, Utah, USA. Preferably the surface of the tape is soft to the touch.

The textured surface on the tape may be provided by having mechanical fasteners. A tape provided with 3M™Dual Lock™ fasteners may be employed to allow contacting regions of the non-adhesive face of the tape to stick together when the cap is engaged with the patient port and/or when the cap is disengaged from the patient port. Use of conventional "hook-and-loop" material is possible, but requires a tape with regions of hook and regions of loop on the non-adhesive face. A preferred tape is 3M™ Dual Lock™ Reclosable fastener SJ4570 low profile clear, available from 3M Tapes and Adhesives group, Bracknell, UK. The features that provide cohesion of the tape are "mushrooms", which are large numbers of small mushroom-shaped features extending away from the non-adhesive surface of the tape. Since the mushrooms interlock, there is no need to have separate types of fastening feature on the same tape. The SJ4570 is provided with Acrylic adhesive for bonding to low energy surfaces. The mushrooms allow the folded tape to be tucked away when the inhaler is not in use, and the act of separating them further cushions the impact applied when the cap is removed.

Suitable medicinal substances for delivery by inhalation, buccal or sublingual delivery in a dispensing device of the invention include those for the treatment of respiratory disorders, e.g., bronchodilators, anti-inflammatories (e.g. corticosteroids), anti-allergics, anti-asthmatics, anti-histamines, and anti-cholinergic agents. Other medicinal substances such as anorectics, anti-depressants, anti-hypertensive agents, anti-neoplastic agents, anti-tussives, anti-anginals, anti-infectives (e.g. antibacterials, antibiotics, anti-virals), anti-migraine drugs, anti-peptics, dopaminergic agents, analgesics, beta-adrenergic blocking agents, cardiovascular drugs, hypoglaecemics, immunomodulators, lung surfactants, prostaglandins, sympathomimetics, tranquilizers, steroids, vitamins, sex hormones, vaccines, therapeutic sense or anti-sense nucleic acids, and other therapeutic proteins and therapeutic peptides may also be employed for delivery by a dispensing device of the invention.

Exemplary medicinal substances which may be employed for delivery by inhalation or for buccal or sublingual delivery include but are not limited to: albuterol, terbutaline, fenoterol, metaproterenol, isoproterenol, isoetharine, bitolterol, epinephrine, tulobuterol, bambuterol, reproterol, adrenaline, ipratropium, oxitropium, tiotropium, daratropium, beclomethasone, betamethasone, flunisolide, budesonide, mometasone, fluticasone, ciclesonide, rofleponide, dexamethasone, prednisone, methylprednisolone, aminophylline, dyphylline, theophylline, cromolyn, nedocromil, ketotifen, azelastine, ergotamine, cyclosporine, salmeterol, formoterol, procaterol, indacaterol, carmoterol, olodaterol, milveterol, vilanterol, abediterol, glycopyrronium, aclidinium, umeclidinium, omalizumab, mepolizumab, montelukast, zafirlukast, zileuton, insulin, atropine, prednisolone, benzphetamine, chlorphentermine, amitriptyline, imipramine, clonidine, actinomycin c, bromocriptine, buprenorphine, pentamidine, calcitonin, leuprolide, alpha1-antitrypsin, interferons, propranolol, lacicortone, triamcinolone, dinoprost, xylometazoline, diazepam, lorazepam, folic acid, nicotinamide, clenbuterol, ethinyloestradiol, levonorgestrel, glyceryl trinitrate, isosorbide dinitrate and pharmaceutically acceptable salts and esters thereof such as albuterol sulfate, formoterol fumarate, salmeterol xinafoate, beclomethasone dipropionate, triamcinolone acetonide, dexamethasone sodium phosphate, dexamethasone acetate, betamethasone sodium phosphate, fluticasone propionate (or furoate), cromolyn siodium, nedocromil sodium, tiotropium bromide, umeclidinium bromide, vilanterol terfenatate, leuprolide acetate and mometasone furoate.

Medicinal containers may be advantageously utilized as part of medicinal dispensing devices for the administration of the above substances through oral, or intranasal delivery. Accordingly, containers fitted with a suitable dosing device may be utilized as canisters, particularly for use in pressurized metered dose inhalers.

For delivery by inhalation, such substances or substances in combination may be administered by inhalation in suspension or in solution in liquefied propellant, in particular liquefied HFA 134a and/or HFA 227, optionally with other excipients.

Alternatively, the substances may be presented in dry powder form in a container that forms part of a DPI. As a further alternative, the substances may be dissolved in an aqueous or solvent-based system for delivery in a portable nebulizer.

Whilst being applicable to pMDIs, the invention herein is also applicable to DPIs and portable nebulizers that have a housing provided with a patient port, for example a mouthpiece or nosepiece, and a cap that can be engaged and disengaged with the patient port to close and open the patient port.

It is to be understood that the present invention covers all combinations of particular, suitable, desirable, favorable, advantageous and preferred aspects of the invention described herein.

EXAMPLES

Figure 1B:
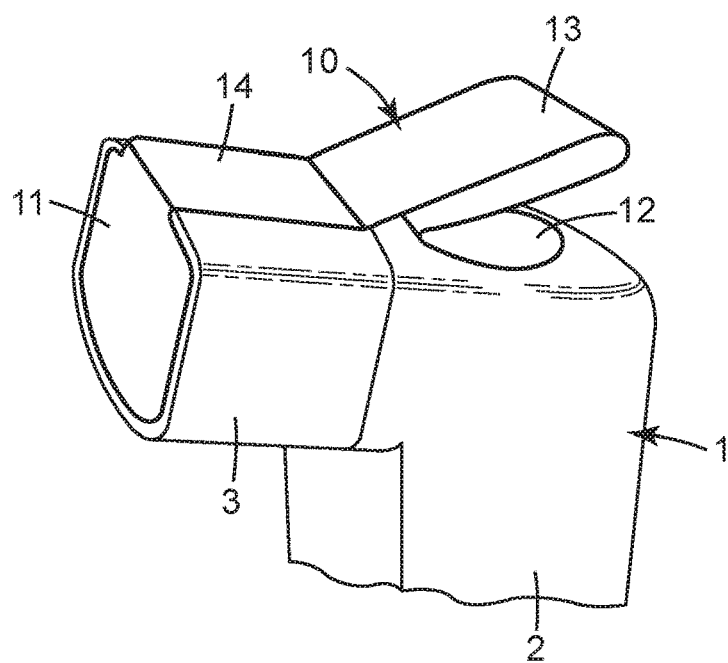

FIGS. 1a and 1b show an inhaler (1) comprising an actuator housing (2) with a cap (3). An adhesive coated portion (12) of the adhesive tape (10) is attached to the base of the actuator by adhesive applied to the corresponding part of the second major face of the tape. Similarly, another adhesive coated portion (14) is attached to the underside of the cap (3) and a further adhesive coated portion (11) is attached to the front of the cap. With the cap in place covering the mouthpiece, the remainder of the tape, i.e. the intermediate portion (13), is folded in three places perpendicular to the length of the tape. Two of these folds are in the uncoated portion of the tape immediately adjacent to the boundaries between the adhesive coating and the uncoated portion, and the third fold is positioned between these two folds (and so is also in the uncoated portion of the tape) to allow the tape to rest flat against the base of the actuator.

Figure 2:
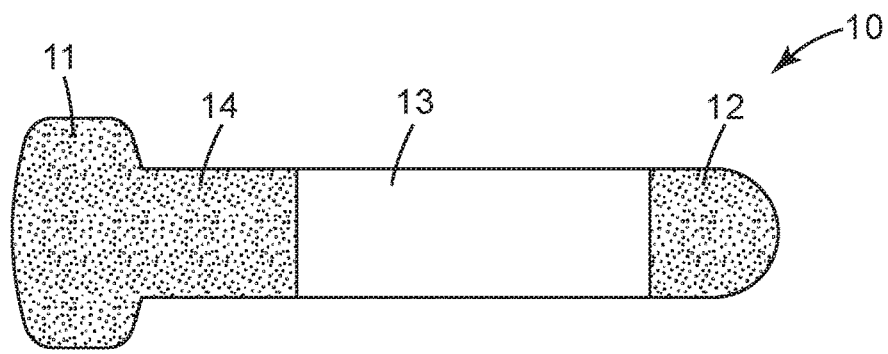
FIG. 2 is a top view of an adhesive tape used in FIG. 1.

FIG. 2 shows the above exemplary tape (10) viewed towards the second major face. It has one end portion (11, 14) coated on one face with adhesive for subsequent attachment to the cap, the other end portion (12) coated on the same face with adhesive for subsequent attachment to the inhaler actuator, and an intermediate uncoated portion (13). The first major face of the tape is not coated with adhesive. The tape is made of a textured PVC reinforced with a scrim of 4 threads per 10 mm longitudinally and 8 threads per 10 mm transversely, portions of the second major face of the tape being coated with adhesive, the main body being 0.4 mm thick and the texture, which is on the non-adhesive face, adding 0.6 mm when uncompressed. The length of the tape is 84.5 mm. The intermediate uncoated portion (13) is 39 mm long and has a width of 14 mm. The lengths of the coated portions are 14.8 mm (11), 16.6 mm (14) and 14.0 mm (12).

The adhesive is 9471LE Laminating Adhesive, available from 3M Tapes and Adhesives group, Bracknell, UK.

Figure 3:
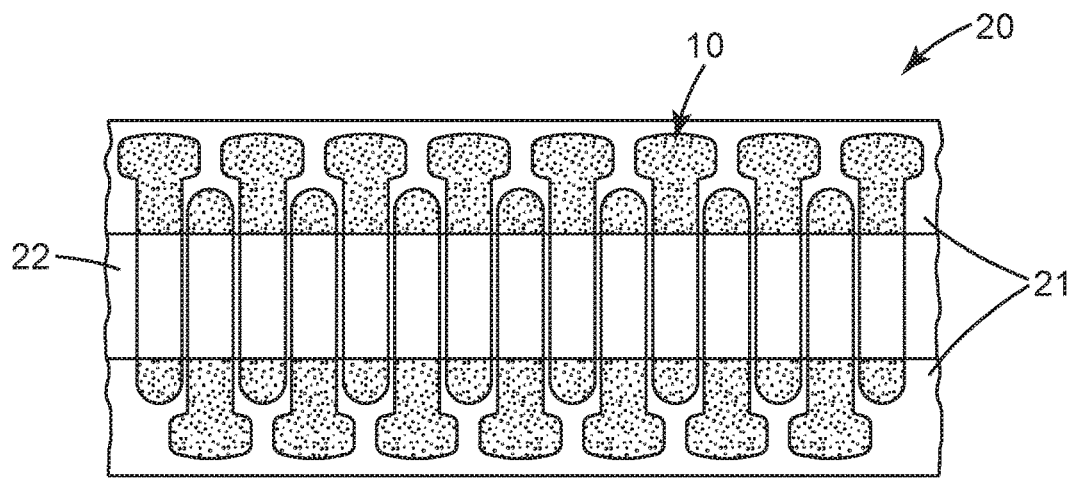
FIG. 3 is a top view of a web used in the manufacture of the adhesive tape of FIG. 2.

FIG. 3 shows a section of web (20) used in the manufacture of adhesive tapes (10). The tape outlines are arranged on the web for maximum utilization of the materials, since the material of the web outside the outlines is discarded. Thus, generally 'T'-shaped tapes are arranged with the stems of the 'T's parallel and 'crosses' of the 'T's alternately above and below the line of stems. The arrangement also serves to align the tapes so that adhesive may be applied to the web in continuous bands (21) across all the tapes, whilst leaving a central intermediate band (22) uncoated with adhesive. The web is overlaid on the adhesive side with a liner, typically a polycoated Kraft paper, or thin polyethylene film.

The technology of web coating is well known in the production of tapes. On a large scale, several of the webs shown in FIG. 3 can be coated with adhesive simultaneously on a much wider web. A liner is then typically laid onto the adhesive from a roll. The much wider web of tape material may be stored on a jumbo roll, then unwound over rollers to a coating station, and thence to a station for applying a liner. The wider web is subsequently slit longitudinally with knives to provide the webs shown in FIG. 3. The individual tapes (10) may be punched out of the webs (20) using cutting tools, while the liner is still attached. The liner is peeled off to provide the tapes of FIG. 2.

Figure 4:
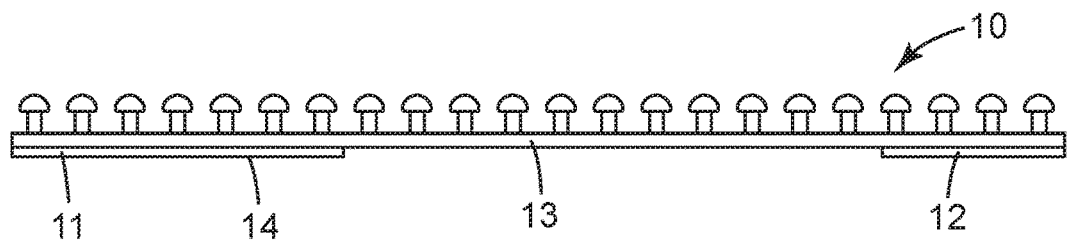
FIG. 4 is a side view of an adhesive tape according to an embodiment of the present disclosure.

FIG. 4 depicts the tape (10) further comprising small mushroom-shaped features (15) extending away from a non-adhesive surface of tape (10). Mushrooms (15) allow tape (10), when folded, to be tucked away when the inhaler is not in use, and the act of separating them further cushions the impact applied when the cap is removed.

The invention claimed is:

1. A dispensing assembly for containing a container filled with a medicinal substance or formulation, said container being suitable for administering the medicinal substance or formulation via inhalation, buccal or sublingual delivery, wherein the dispensing assembly comprises a housing defining a patient port through which, in use, said medicinal substance or formulation is dispensed, wherein the dispensing assembly further comprises a cap that can be engaged with and disengaged from the patient port to close and open the patient port, and a pressure sensitive adhesive tape having one portion affixed to the housing and a second portion affixed to the cap, so that when the cap is disengaged from the patient port, the cap is still connected to the housing, wherein the pressure sensitive adhesive tape has a first major face that is free from adhesive, and wherein the first major face has a surface texture and mechanical fasteners selected from the group consisting of two regions of complementary mechanical fasteners and male-male mechanical fasteners.

2. The dispensing assembly as in claim 1 in which the pressure sensitive adhesive tape comprises an applied adhesive, wherein the adhesive, when composed into a prepared specimen and tested according to ASTM D3330 method E modified to use a 90° peel to separate one face of the adhesive from a specified stainless steel panel, the opposing face of the adhesive attached to a 51 micron aluminum backing and the prepared specimen stood for a 15 minute dwell time at room temperature prior to testing, exhibits a peel adhesion of at least 40 N per 100 mm width of sample.

3. The dispensing assembly as in claim 2 wherein the adhesive exhibits a peel adhesion of at least 60 N per 100 mm width of sample.

4. The dispensing assembly as in claim 3 wherein the adhesive exhibits a peel adhesion of at least 75 N per 100 mm width of sample.

5. The dispensing assembly as in claim 4 wherein the adhesive exhibits a peel adhesion of at least 80 N per 100 mm width of sample.

6. The dispensing assembly as in claim 1 in which the adhesive is an Acrylic adhesive.

7. The dispensing assembly as in claim 6 in which the adhesive comprises a tackifier as a starting material.

8. The dispensing assembly as in claim 6 in which the adhesive has a glass transition temperature in the range 0° C. to 10° C.

9. The dispensing assembly as in claim 6 in which the adhesive is a closed cell adhesive foam.

10. The dispensing assembly as in claim 1 in which the portions of the tape are end portions and the tape has an intermediate portion between the two end portions to which no adhesive is applied.

11. The dispensing assembly as in claim 10 in which the intermediate portion has at least one fold line to allow the tape to fold when the cap is engaged with the patient port.

12. The dispensing assembly as in claim 1 in which the first major face is provided with male-male mechanical fasteners.

13. The dispensing assembly as in claim 1 in which the first major face has two regions of complementary mechanical fasteners.

14. The dispensing assembly as in claim 1 wherein said container is a pressurized metered dose inhaler canister.

15. The dispensing assembly as in claim 1 wherein said container contains dry powdered medicinal substance or formulation.

16. A dispensing device comprising a dispensing assembly according to claim 1 and a container.

17. The dispensing device as in claim 16 which is a pressurized metered dose inhaler.

18. The dispensing device as in claim 16 which is a dry powder inhaler.

* * * * *

UNITED STATES PATENT AND TRADEMARK OFFICE
CERTIFICATE OF CORRECTION

PATENT NO. : 10,265,484 B2
APPLICATION NO. : 14/430710
DATED : April 23, 2019
INVENTOR(S) : Adam Stuart et al.

Page 1 of 1

It is certified that error appears in the above-identified patent and that said Letters Patent is hereby corrected as shown below:

In the Specification

Column 3
Line 19, delete "etc.," and insert -- etc. --, therefor.
Line 56, delete "polyamids" and insert -- polyamides --, therefor.

Column 4
Line 34, delete "Kristalex3100" and insert -- Kristalex 3100 --, therefor.

Column 6
Line 46, delete "3M™Dual" and insert -- 3M™ Dual --, therefor.

Column 7
Line 9, delete "hypoglaecemics," and insert -- hypoglycemics, --, therefor.
Line 33, delete "alpha1-" and insert -- alpha-1- --, therefor.
Line 43, delete "siodium," and insert -- sodium, --, therefor.
Line 44, delete "terfenatate," and insert -- trifenatate, --, therefor.

Signed and Sealed this
Third Day of September, 2019

Andrei Iancu
*Director of the United States Patent and Trademark Office*